US00PP12082P2

(12) United States Plant Patent
Deroose

(10) Patent No.: US PP12,082 P2
(45) Date of Patent: Sep. 11, 2001

(54) GUZMANIA PLANT NAMED 'SIRALBERT'

(75) Inventor: Reginald Deroose, Evergem (BE)

(73) Assignee: Deroose Plants BVBA, Evergem (BE)

( * ) Notice: Subject to any disclaimer, the term of this patent is extended or adjusted under 35 U.S.C. 154(b) by 0 days.

(21) Appl. No.: 09/419,916

(22) Filed: Oct. 18, 1999

(51) Int. Cl.[7] ..... A01H 5/00
(52) U.S. Cl. ..... Plt./371
(58) Field of Search ..... Plt./371

(56) References Cited

U.S. PATENT DOCUMENTS

P.P. 9,476 * 3/1996 Kent ..... Plt./371
P.P. 10,069 * 10/1997 Kent ..... Plt./371
P.P. 10,383 * 5/1998 Bos ..... Plt./371

OTHER PUBLICATIONS

GTITM UPOVROM Citation for 'Sir Albert' as per QZ PBR 991056; Jul. 21, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A Guzmania plant named 'Siralbert' characterized by vigorous growth habit; variegated foliage, from one-third to one-half of the leaf surface, which goes from red-purple at the sheath to cream-white towards the apex of the leaf; margins are dark-purple at the leaf sheath and become dark-green towards the apex of the leaf; rather compressed inflorescence where the primary bracts are positioned bracts with yellow-orange color and red to reddish-pink striations; and erect arching leaves with no droop at the apex.

1 Drawing Sheet

BACKGROUND OF THE INVENTION

The present invention comprises a new and distinct cultivar of Guzmania plant, hereinafter referred to by the cultivar name 'Siralbert'. The genus Guzmania is a member of the family Bromeliaceae.

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Desirably, the plants are shaded from direct sunlight, and during the spring to autumn period, the central vase-like part of the leaf rosette is desirably filled with water.

Guzmania is native to tropical America. Leaves of Guzmania are usually formed as basal rosettes, which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots produced by the plant which may then be rooted. The resulting plantlets are detached from the mother plant and may be potted in a suitable growing mixture.

The new cultivar was discovered as a naturally occurring mutation among plants of the parent cultivar 'Gisela G26' (unpatented), which is a non-variegated Guzmania plant.

The female parent of 'Gisela G26' was Guzmania 'Magnifica' (unpatented). The male parent of 'Gisela G26' was *Guzmania zahnii*. 'Siralbert' was discovered and selected among plants of the cultivar 'Gisela G26' by the inventor. Reginald Deroose, in 1990 in a controlled environment in Evergem, Belgium.

'Siralbert' is characterized by its vigorous growth, its variegated foliage which is red-purple at the sheath to creamy white towards the apex of the leaf, and its rather compressed inflorescence where the primary bracts are positioned with yellow to orange color and red to reddish-pink striations.

The first act of asexual reproduction of the new cultivar was performed by the inventor in 1990, from offshoots produced by the plant. Horticultural examination of these asexually reproduced plants initiated in 1990 has demonstrated that the combination of characteristics as herein disclosed for 'Siralbert' are firmly fixed and reproduces true to type through successive generations of asexual reproduction.

BRIEF DESCRIPTION OF THE INVENTION

The following traits have been repeatedly observed and are determined to be basic characteristics of 'Siralbert' which is combination distinguish this Guzmania as a new and distinct cultivar:

1. Vigorous growth habit;

2. Variegated foliage, from one-third to one-half of the leaf surface, which goes from red-purple at the sheath to cream-white towards the apex of the leaf;

3. Margins are dark-purple at the leaf sheath and become dark-green towards the apex of the leaf;

4. Rather compressed inflorescence where the primary bracts are positioned, bracts with yellow-orange color and red to reddish-pink striations; and 5. Erect arching leaves with no droop at the apex.

'Siralbert' has not been observed under all possible environmental conditions. The phenotype of the new cultivar may vary significantly when grown under different conditions of temperature, light and other determining factors, without any change in genotype.

Of the many commercial cultivars known to the inventor, the most similar in comparison to 'Siralbert' is the parental cultivar Guzmania 'Gisela G26' and 'Symfonie Encore', U.S. Plant patent application Ser. No. 09/432,079. The inflorescence and plant shape of 'Siralbert' are similar to the inflorescence and plant shape of 'Gisela G26'. However, the leaves of 'Siralbert' are variegated whereas 'Gisela G26' has entirely green leaves. The leaves of 'Siralbert' are erect-arching whereas 'Giseala G26' has more downward-bending leaves. 'Siralbert' differs from 'Symfonie Encore' in that plants of 'Siralbert' grow shorter and smaller than those of 'Symfonie Encore'. 'Siralbert' has a smaller (in width) leaf sheath, shorter leaf length and smaller (in width) leaf blade than 'Symfonie Encore'. The leaf variegation of 'Siralbert' is distinctly less wide than 'Symfonie Encore'. The leaves of 'Siralbert' are erect and arch with no droop. The leaves of 'Symfonie Encore' are erect with a well-defined droop at the last 11–18 cm of the blade. The inflorescence of 'Siralbert' is smaller, less straight, and has less intense contrasting color than 'Symfonie Encore'.

BRIEF DESCRIPTION OF THE DRAWING

The accompanying photographic illustration shows a perspective view of the foliage and inflorescence characteristics of a typical 'Siralbert' plant following growth under appropriate growing conditions, with colors being as true as possible with illustrations of this type.

DETAILED BOTANICAL DESCRIPTION

The following observations, measurements and values describe plants grown in Evergem, Belgium, under greenhouse conditions which closely approximate those generally used in horticultural practice. The plant described is approximately 13 months old from a 25 cm long cutting, for a plant height of 50 cm (including 10 cm pot). Color references are made to The Royal Horticultural Society Color Chart (R.H.S.), except where general colors of ordinary significance are used.

Classification:

*Commercial.*—Guzmania c.v. 'Siralbert'.

Species: Guzmania 'Siralbert' is a naturally occurring mutation of Guzmania 'Gisela G26'; Guzmania 'Gisela G26' is Guzmania 'Magnifica' (cultivar of *G. lingulata* v. *Cardinalis*×*lingulata minor*)×*Guzmania zahnii.*

Parentage: Naturally occuring mutation of Guzmania 'Gisela G26'.

Propagation: Vegetative, by removal of offsets.

Plant:

*Form.*—Funnel-form rosette.

*Height.*—Approximately 45–50 cm when in full bloom.

*Diameter.*—Approximately 80–90 cm.

*Growth habit.*—Vigorous, it takes approximately 13 months to produce a finished flowering plant from a 25 cm long cutting, in a standard heated greenhouse with temperatures during the day of 20 degrees Celsius, and 18 degrees Celsius at night.

Foliage:

*Habit.*—Arcuate spreading, leaves are slightly erect towards the center of the plant. Lowest leaves are at an angle of 45° to 55°, bending downward from the middle. Upper leaves are at an angle of 40° to 45° to slightly bending downward at the tip.

*Size.*—Approximately 40–50 cm long.

*Leaf sheaths.*—Elliptic shape glabrous surface margins are entire dark-green (RHS 147A) to dark-purple (RHS 187A); center is red-purple (RHS 60B) with dark-green and dark-purple striations (all color designations are for both upper and lower surfaces).

*Leaf blades.*—Ligulate, acute to attenuate apex 2.5–4.0 cm wide, variegated from one-third to one-half of the leaf surface. Margins are dark-green (RHS 147A); center is white to cream (RHS 155A–158A) with dark-green, irregular striations. The variegation is pointed upward to the apex of the leaf. (Color designations represent both upper and lower surfaces).

*Scape.*—Round, approximately 45–50 cm long and 1 cm in diameter.

*Scape bracts.*—Approximately 10, acute to attenuate apex, margin entire, glabrous surface, densely imbricate, foliaceous, concealing the scape, little arching, 1.5–3.0 cm wide, variegation similar to the leaves. The central zone goes from red-purple (RHS 63A) to orange-yellow (RHS 10C–18A) (all color designations are for both upper and lower surfaces).

*Number of leaves.*—Approximately 30 to 40.

Inflorescence:

*Habit.*—Compressed where the primary bracts are positioned to compact shaped with approximately 15–20 sprialley arranged bracts; approximately 9–12 cm in diameter.

*Primary bracts.*—Approximately 20, elliptic shape, margin is entire, sessile base, apex is acute to attenuate, 2.0–8.0 cm long and 0.5–3.5 cm wide; orange-yellow (RHS 11A–13A) with red striations (RHS 39A to a color that varies between RHS 47B and RHS 47C), the lower surface is red (RHS 53C).

*Floral bracts.*—1 floral bract per flower, elliptic shape; cucullate apex; sessile base; margin is entire, approximately 1–2 cm wide; floral bracts are closely folded around the flowers; 1.5–2.5 cm long, yellow (RHS color varying between 7A and 7B) (Both surfaces).

*Flowers.*— Sepals: 3 elliptic shaped, acute apex, sessile base, margin entire, approximately 1.5–2 cm long, 0.5 cm wide, yellow (RHS 3A) (Both surfaces). Petal: 3 partially fused at base, free part: elliptic shape, margin entire, approximately 0.8–1.2 cm long, 3–5 cm wide, obtuse apex, yellow (RHS 7A) (Both surfaces).

*Flower diameter/length.*—5 mm diameter, 1–1.5 cm long.

*Buds.*—Elliptic shape, approximately 1.5–2 cm long, 4–5 mm diameter, yellow (RHS 7A).

*Duration of flowers.*—Individual flowers last for one day and the total duration of flowering is approximately 12 weeks.

Reproductive organs: Anthers 1 cm long; lower parts of filaments fused with corolla, 6 per flower, color RHS 15C; style 1 cm long, 3-lobed pistil, 1 per flower, color RHS 15C.

Other significant characteristics: The inflorescence holds its color for approximately 5–7 months.

Pollen: No known pollen produced.
Fruit: No fruit produced.
Disease/pest/resistance susceptibility: No specific resistance or susceptibility observed.

I claim:

1. A new and distinct Guzmania plant named 'Siralbert', substantially as illustrated and described herein.

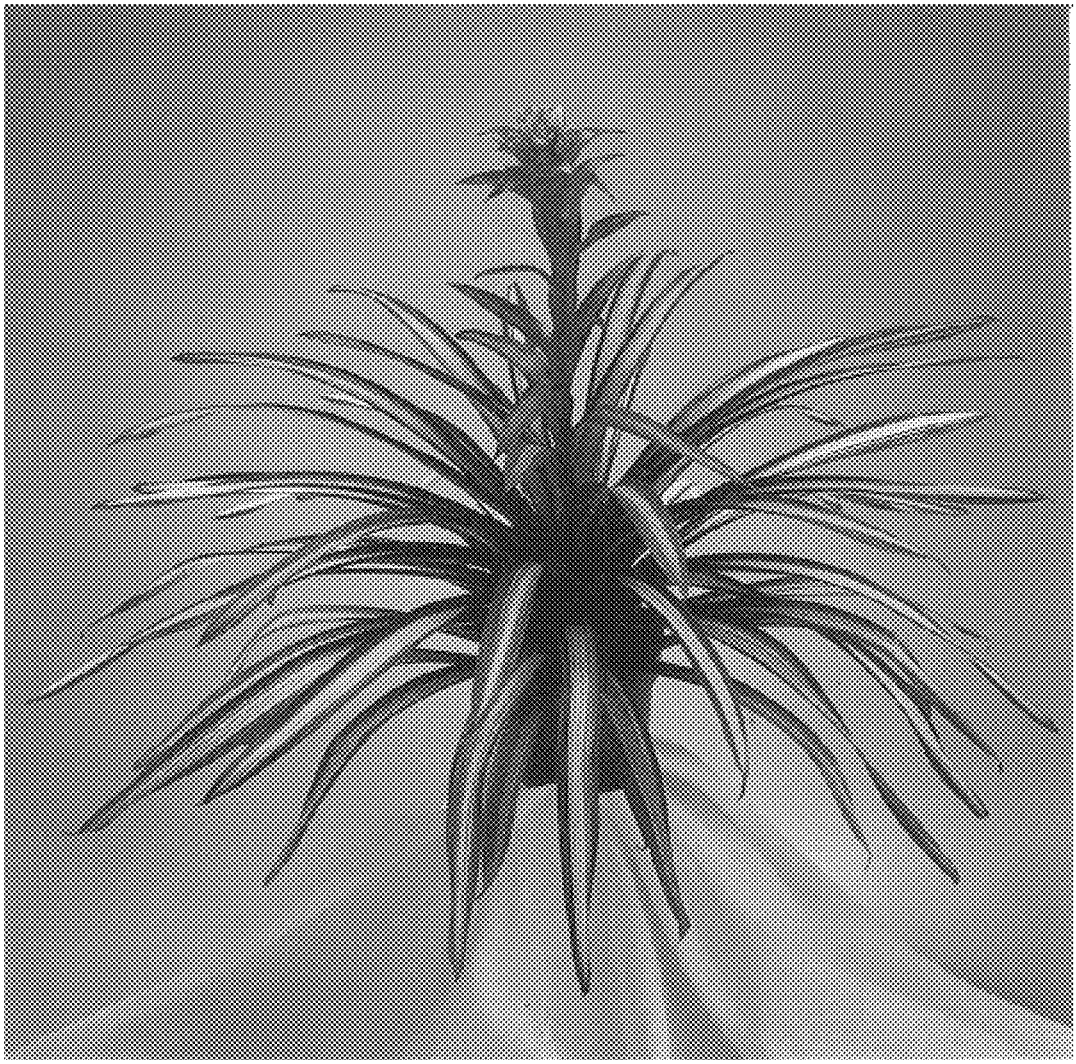

* * * * *